United States Patent [19]

Mikkelsen

[11] Plant 4,205

[45] Jan. 31, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,531

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel impatiens variety having a strong, rigid, arching growth habit and an attractive contrast between the variegated foliage and large pink blossoms.

1 Drawing Figure

1

The present invention relates to a new and distinctive cultivar of Impatiens plant, botanically known as Impatiens, and referred to by the cultivar name Liberty, developed by me through controlled breeding by crossing the unpatented seedline 74–214–4 (Mikkelsen) (seed parent) with the unpatented Seedling 74–197–11 (Mikkelsen) (pollen parent). Asexual reproduction of terminal or stem cuttings taken by me in Ashtabula, Ohio has shown that the unique features of this new Impatiens are stabilized and are reproduced true to type in successive propagations.

The following characteristics distinguish the new Impatiens from both its parent varieties and other cultivated Impatiens of this type known and used in the floriculture industry.

1. In mature plants the terminal whorl of leaves develops very close to the previous node; flowering often occurs at several nodes on the same stem at the same time giving a very floriferous appearance.

2. The top and two bottom petals develop a near white throat at their bases; the two side petals are less distinct in this characteristic.

3. The wide leaves have a broad area of cream to light yellow variegation surrounding the mid vein.

4. The color contrast of the foliage and flowers is distinct and attractive.

5. The plant has strong rigid growth that develops more to an arching flowing pattern rather than straight up formal growth.

6. Flower size is above average for this series of new hybrids, measuring up to 6.5 to 7 cm. in diameter.

7. Top petal is largest, being up to 4 cm. across, with the two side petals being smallest, and up to 2.5 cm. across.

8. Cutting production from stock plants is above average on mature plants because of the closeness of the terminal internodes.

9. This hybrid should be grown in a very lightly shaded environment to prevent spotting of the light variegated area in the leaves. By way of contrast, most New Guinea hybrids developed during my current breeding program can be grown in full sunlight.

10. Flower color is similar to the cultivar Preamble in winter, but not in summer when Preamble is pink. Preamble is disclosed in my pending application Ser. No. 764,024 filed Jan. 31, 1977.

The accompanying colored photograph illustrates the overall appearance of the new cultivar and shows the colors thereof as true as it is reasonably possible to obtain in a colored reproduction of this type.

2

The following is a detailed description of my new Impatiens cultivar based on plants produced under commercial practices in greenhouses at Mikkelsens Inc., Ashtabula, Ohio, and flowering in November, 1976. Color references are made to the Royal Horticultural Society Colour Chart except where general terms of ordinary dictionary significance are used.

Parentage: A controlled pollination of Mikkelsen seedling 74–214–4 as the seed parent crossed with Mikkelsen seedling 74–197–11 as the pollen parent.

Propagation:

*Type cutting.*—Tip or stem cuttings 2–3 cm. long.

*Time to visible rooting.*—10 days at 21° C summer, and 15 days at 20° C winter.

*Rooting habit.*—Typical for New Guinea Impatiens; rapid very profuse in both primary and secondary roots, dendritic.

Plant description:

*Form.*—Side branches have an arching flare to give a graceful placement appearance.

*Habit of growth.*—Heavy, rigid arching, side shoot growth, internodal space 5–6 cm., slow to medium rate of growth.

*Foliage.*—Highly variegated, symmetrical. Size: 5–6 cm. wide by 12–15 cm. long with petiole 3 cm. long, so that some leaves may be up to 18 cm. from base of petiole to apex. Shape: symmetrically elliptical, apex acuminate, base cuneate, generally flat. Texture: Firm, leathery, glabrous, rugose. Margin: Nearly entire, quite ciliolate. Color: Young foliage, top side: outer area green 137A-B, inner area yellow orange 21-B; under side: outer area yellow green 146-B, inner area 21-C. Mature foliage, top side: outer area green 137B-C, inner area cream yellow; under side: outer area yellow green 147B-C, inner area yellow orange 18B-C. Venation: pinnately, arcuate.

Flowering description:

*Flowering habit.*—Flowering is sequentially around the whorl of leaves on a one to one ratio of flowers to leaves; often 6 to 8 flowers in bloom at one time at each whorl.

*Natural flowering season.*—Flowering is indeterminate, occurs all year around but distinctly more flowering in the late fall, winter and spring than in summer.

*Flower buds.*—Immature, symmetrically conical, with two true sepals, and a scale-like sepal on the back of the top petal. A hollow spur emerges from the interior as the bud develops.

*Flowers borne.*—Individually on a pedicel light red to pink in color 5–6 cm. long and 2 mm. in diameter at the base. Flowering is sequentially around the whorl of leaves but uniformly in a short period of time.

*Quantity of flowers.*—Typical for New Guinea Impatiens but appears highly floriferous because of quantity in flower at one time.

*Petals.*—Shape: Top petal very large, up to 4 cm. in diameter, two side petals frequently display several indentations on the top lobes, all five petals have indented apices with top petal apex drawn backwards by the scale like sepal. Color: Top side in winter when opening near 44D or 43C, fading to quite stable 44D; under side red 41C. Number of petals: 5; one top petal side petals and two bottom petals with light throat. Spur is nearly circular in early stages, developing to curve 6 cm. long and is red 53A.

*Reproductive organs.*—Stamens: One in number. Anther shape: Hooded over pistil, color somewhat darker than petals red 44C. Pollen color: Dull or flat white. Pistils: Stigma shape: Flat, circular, irregular surface. Style: Translucent green in color. Ovaries: One, 4–5 mm., dark green in color.

I claim:

1. A new and distinct cultivar of Impatiens known by the cultivar name Liberty and particularly as to uniqueness by the combined characteristics of a very floriferous appearance due to the terminal whorl of leaves developing close to the previous node and branching frequently at several nodes on the same stem; the top and bottom petals having a nearly white throat at the base; relatively wide and variegated leaves; generally pink flower color and above average flower size; strong, rigid growth which develops an arching, flowering pattern; ease of propagation in quantity, and preferred growth in a very lightly shaded environment.

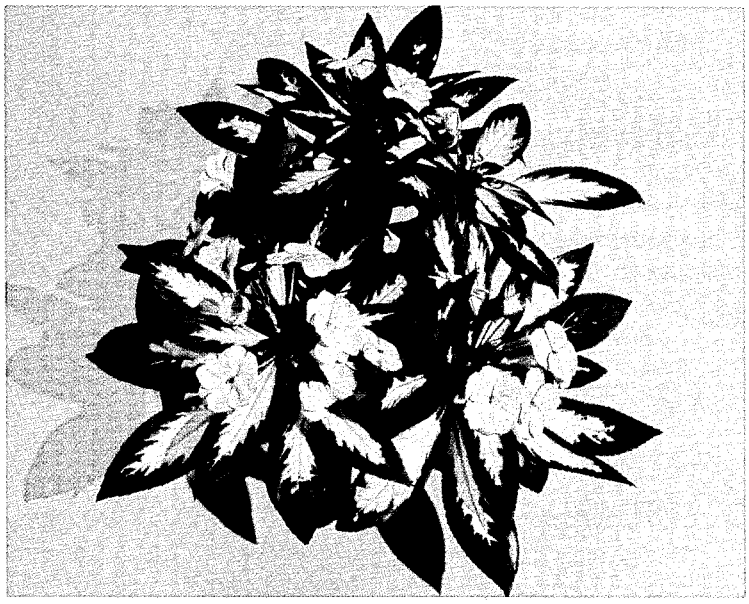

* * * * *